United States Patent
Meftah et al.

(10) Patent No.: US 11,351,007 B1
(45) Date of Patent: Jun. 7, 2022

(54) SURGICAL SYSTEMS WITH INTRA-OPERATIVE 3D SCANNERS AND SURGICAL METHODS USING THE SAME

(71) Applicant: CAIRA Surgical, New York, NY (US)

(72) Inventors: Morteza Meftah, New York, NY (US); Irina Benimovich, New York, NY (US)

(73) Assignee: CAIRA SURGICAL, New York, NY (US)

( * ) Notice: Subject to any disclaimer, the term of this patent is extended or adjusted under 35 U.S.C. 154(b) by 0 days.

(21) Appl. No.: 16/254,220

(22) Filed: Jan. 22, 2019

Related U.S. Application Data

(60) Provisional application No. 62/620,448, filed on Jan. 22, 2018.

(51) Int. Cl.
*A61B 90/00* (2016.01)
*A61B 34/10* (2016.01)
*A61B 17/15* (2006.01)

(52) U.S. Cl.
CPC ............ *A61B 90/37* (2016.02); *A61B 17/155* (2013.01); *A61B 17/157* (2013.01); *A61B 34/10* (2016.02); *A61B 2034/107* (2016.02); *A61B 2090/366* (2016.02); *A61B 2090/373* (2016.02)

(58) Field of Classification Search
CPC ... A61B 5/0037; A61B 17/155; A61B 17/157; A61B 17/56; A61B 2017/564; A61B 34/10; A61B 2034/107; A61B 2034/108; A61B 2090/364; A61B 2090/366; A61B 90/37; A61B 2090/373
See application file for complete search history.

(56) References Cited

U.S. PATENT DOCUMENTS

| | | |
|---|---|---|
| 5,604,485 A | 2/1997 | Lauro et al. |
| 7,549,960 B2 | 6/2009 | Govari |
| 7,783,099 B1 | 8/2010 | Stefan et al. |

(Continued)

FOREIGN PATENT DOCUMENTS

| | | |
|---|---|---|
| EP | 2996555 A2 | 3/2016 |
| WO | 2008063249 A2 | 5/2008 |

(Continued)

OTHER PUBLICATIONS

Merkl, Brandon C., "The Future of the Operating Room: Surgical Preplanning and Navigation Using High Accuracy Ultra-Wideband Positioning and Advanced Bone Measurement." University of Tennesse, Knoxville, Dec. 2008.

(Continued)

*Primary Examiner* — Matthew J Lawson
(74) *Attorney, Agent, or Firm* — MH2 Technology Law Group, LLP

(57) ABSTRACT

Aspects of the present disclosure include surgical systems that provide a cost-effective, accurate, and efficient system for performing surgical procedures. In one aspect of the disclosure, a surgical system utilizes an intra-operative 3D scanner that can be used to determine anatomical landmarks and calculate surgical positions based on such anatomical landmarks. In some examples, aspects of the present disclosure also include providing guidance information for guiding the placement of a surgical instrument according to the calculated surgical positions.

18 Claims, 9 Drawing Sheets

(56) References Cited

U.S. PATENT DOCUMENTS

| | | | |
|---|---|---|---|
| 8,717,430 | B2 | 5/2014 | Simon et al. |
| 9,220,570 | B2 | 12/2015 | Kim et al. |
| 9,467,118 | B2 | 10/2016 | Zhou |
| 9,498,647 | B2 | 11/2016 | Kantrowitz et al. |
| 10,205,238 | B1 | 2/2019 | Wurmfeld |
| 2002/0107445 | A1 | 8/2002 | Govari |
| 2002/0143320 | A1 | 10/2002 | Levin |
| 2004/0068187 | A1 | 4/2004 | Krause et al. |
| 2006/0094958 | A1 | 5/2006 | Marquart et al. |
| 2007/0197891 | A1 | 8/2007 | Shachar et al. |
| 2007/0225595 | A1 | 9/2007 | Malackowski et al. |
| 2008/0154389 | A1 | 6/2008 | Smith et al. |
| 2009/0005708 | A1 | 1/2009 | Johanson et al. |
| 2010/0085156 | A1 | 4/2010 | Tucker |
| 2010/0137712 | A1 | 6/2010 | Krag et al. |
| 2011/0180609 | A1 | 7/2011 | Sato et al. |
| 2013/0172907 | A1 | 7/2013 | Harris |
| 2014/0200621 | A1 | 7/2014 | Malackowski et al. |
| 2015/0196369 | A1 | 7/2015 | Glossop |
| 2016/0360997 | A1 | 12/2016 | Yadav et al. |
| 2016/0361101 | A1 | 12/2016 | Moctezuma de la Barrera et al. |
| 2017/0095294 | A1 | 4/2017 | Gantes |
| 2017/0143494 | A1* | 5/2017 | Mahfouz ............... A61B 90/06 |
| 2017/0239013 | A1 | 8/2017 | Frame et al. |
| 2017/0312035 | A1 | 11/2017 | May et al. |
| 2019/0192072 | A1 | 6/2019 | Bailey et al. |
| 2019/0350518 | A1 | 11/2019 | Bailey et al. |
| 2019/0380792 | A1 | 12/2019 | Poltaretskyi et al. |
| 2020/0000366 | A1 | 1/2020 | Katabi et al. |
| 2020/0138518 | A1* | 5/2020 | Lang ..................... A61B 90/37 |
| 2020/0170751 | A1 | 6/2020 | Pack et al. |
| 2020/0237441 | A1 | 7/2020 | Zuhars et al. |
| 2021/0077198 | A1 | 3/2021 | Meftah |
| 2021/0077199 | A1 | 3/2021 | Meftah |
| 2021/0080563 | A1 | 3/2021 | Meftah |
| 2021/0153946 | A1 | 5/2021 | Bonny et al. |

FOREIGN PATENT DOCUMENTS

| | | |
|---|---|---|
| WO | 2011136986 A1 | 11/2011 |
| WO | 2016199051 A1 | 12/2016 |
| WO | 2017185170 A1 | 11/2017 |

OTHER PUBLICATIONS

Growshapes Biomedical Case Study. http://www.growshapes.com/uploads/2/5/6/0/25608031/casestudy_biomedical (May2015).

Staff News Brief, "White Light Scanner—Alternative to CT for Assessment of Pediatric Chest Deformities?" http://appliedradiology.com/articles/white-light-scanner-alternative-to-ct-for-assessment-of-pediatric-chest-deformities (Jun. 7, 2016).

Vorum, Medical Expo. http://www.medicalexpo.com/prod/vorum/product-104119-761593.html (Last viewed Jan. 28, 2019).

https://www.youtube.com/watch?v=ibkmvfoN8LY. 3D Scan: Knee Scan With BodyScan (Published on Dec. 3, 2014; Last viewed Jan. 28, 2019).

Pecheva et al., "White Light Scanning Interferometry Adapted for Large-Area Optical Analysis of Thick and Rougth Hydroxyapatite Layers." https://www.ncbi.nlm.nih.gov/pubmed/17295521 (Mar. 27, 2007; Epub Feb. 13, 2007).

3D Bone Models by CinZara. https://www.cinzara.com/services/3d-bone-models/ Copyright 2017(Last viewed on Jan. 28, 2019).

Thomas et al., "3D Printing for Reconstructive Surgery." Woodhead Publishing Series in Biomaterials. (https://books.google.com/books?id=tEiZDgAAQBAJ&pg=PA42&lpg=PA42&dq=white+light+scanner+surgery&source=bl&ots=jBlgjUGWgt&sig=uQ4ZVNx9MoEpiSv3E0x5gMiDBI&hl=en&sa=X&ved=0ahUKEwiVzLDO0c7YAhVC02MKHbyhBN0Q6AEllgEwDQ#v=onepage&q=white%20light%20scanner%20surgery&f=false)(2018).

Office Action issued in U.S. Appl. No. 17/068,978 dated Dec. 24, 2020, 11 pages.

Office Action issued in U.S. Appl. No. 17/068,978 dated Apr. 6, 2021, 8 pages.

Notice of Allowance issued in U.S. Appl. No. 17/068,978 dated Jun. 23, 2021, 9 pages.

Office Action issued in U.S. Appl. No. 16/573,095 dated Jul. 30, 2021, 16 pages.

Office Action issued in U.S. Appl. No. 17/017,015 dated Oct. 27, 2021, 29 pages.

International Search Report and Written Opinion issued in International Patent Application No. PCT/US2021/021863 dated Sep. 6, 2021, 20 pages.

* cited by examiner

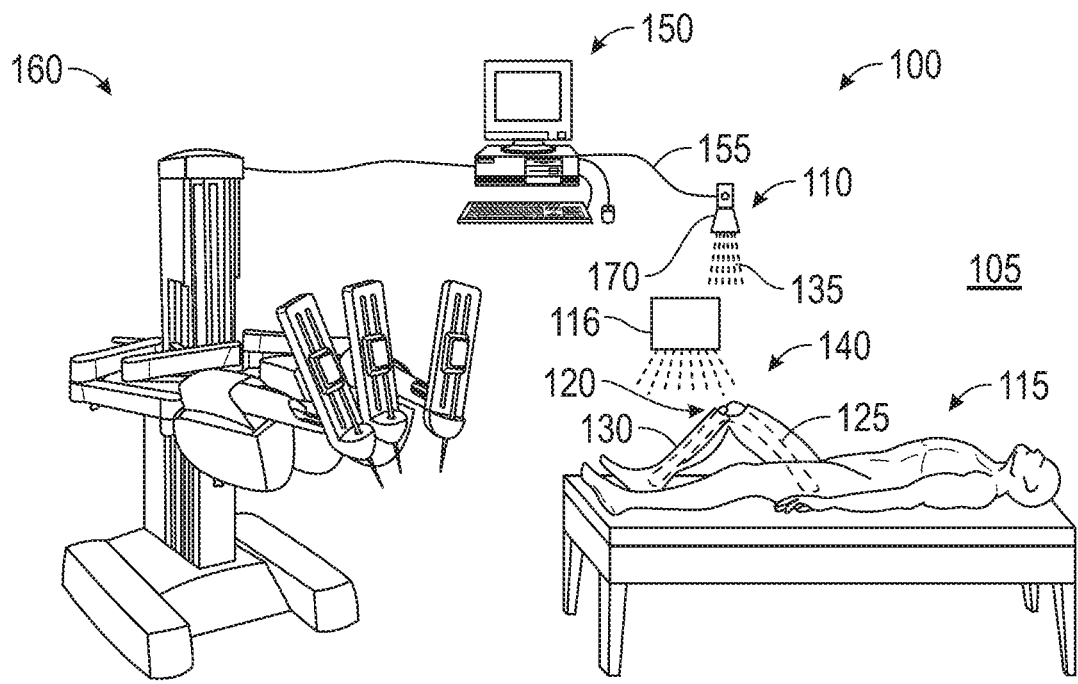
FIG. 1A
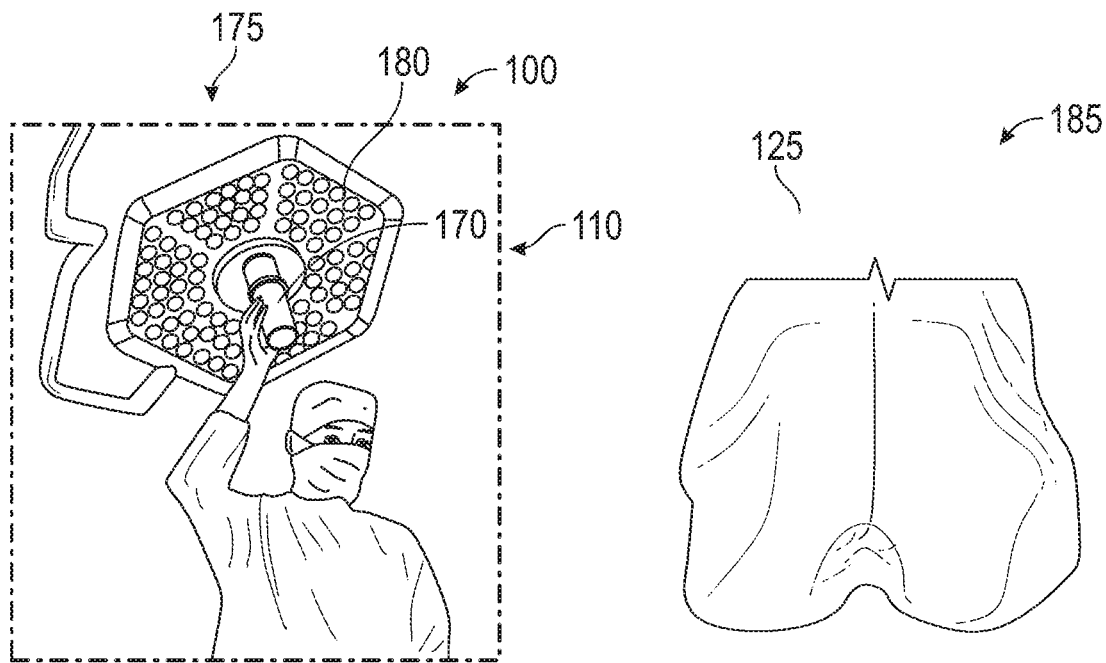
FIG. 1B
FIG. 1C

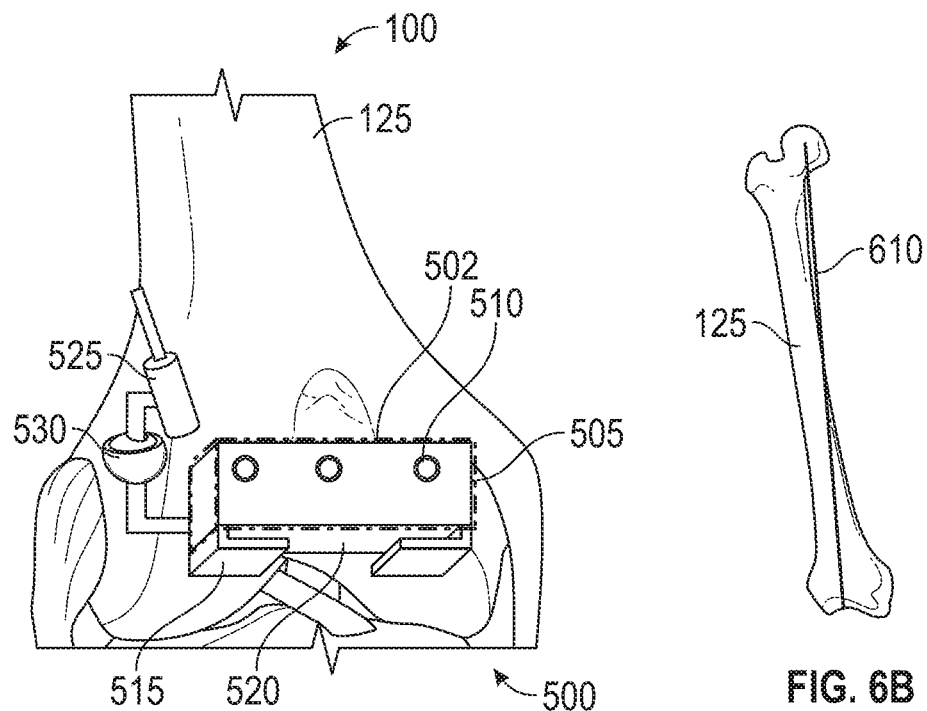
FIG. 6A
FIG. 6B
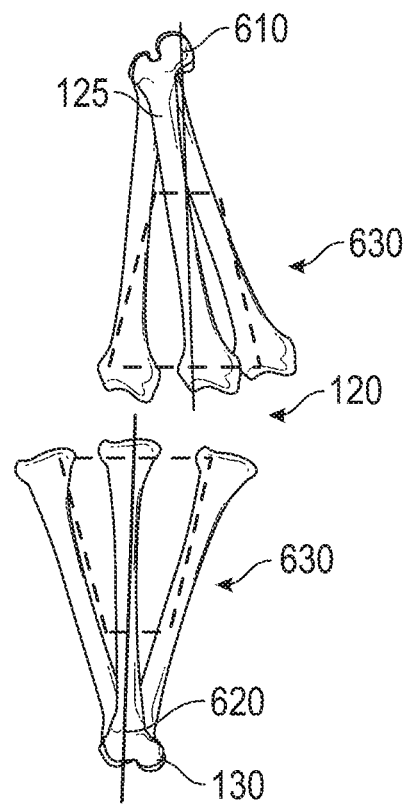
FIG. 6C

SURGICAL SYSTEMS WITH INTRA-OPERATIVE 3D SCANNERS AND SURGICAL METHODS USING THE SAME

RELATED APPLICATION DATA

This application claims the benefit of priority of U.S. Provisional Patent Application Ser. No. 62/620,448, filed Jan. 22, 2018, and titled "Surgical System With Intra-Operative 3D Scan," which is incorporated by reference herein in its entirety.

FIELD OF THE INVENTION

The present invention generally relates to the field of surgical systems. In particular, the present invention is directed to surgical systems with intra-operative 3d scanners and surgical methods using the same.

BACKGROUND

Joint replacement surgery has become an ever-increasing area of surgical procedures. It has been reported that more than 7 million Americans living with a hip or knee replacement. A 2017 report of American Joint Registry shows 860,080 procedures from 654 institutions and 4,755 surgeons, representing a 101% increase in procedures from the year prior. Kurt et al in an article in the Journal of Bone and Joint Surgery estimate that 700,000 knee replacement procedures are performed annually in the US, and this number is projected to increase to 3.48 million procedures per year by 2030. The current annual economic burden of revision knee surgery is $2.7 billion for hospital charges alone, according to Bhandari et al in Clinical Medical Insights: Arthritis and Musculoskeletal Disorders (2012). By 2030, assuming a 5-fold increase in the number of revision procedures, this economic burden will exceed $13 billion annually (Bhandari et al). Adding to the number of the procedures and the economic burden is the fact that of the total knee replacements per annum, around 3% need to be revised for malposition/malalignment. This constitutes more than 21,000 cases a year of patients suffering who need to undergo a revision surgery.

Currently there are two ways of performing a knee replacement, either with conventional instruments or computer aided surgery. Most cases in the United States are performed using conventional instruments. This method involves using intra- or extra-medullary rods to reproduce the anatomic axes. For the proximal tibial cut, an extramedullary rod is conventionally used. The distal portion of the rod is clamped around the ankle and the tibia is cut perpendicular to the anatomical axis. For the distal femoral cut, an intra-medullary rod is also conventionally used. The femur is drilled to accept the rod and then the distal femur is arbitrarily cut at 5 degrees, with a range of 3 to 7 degrees. The rotational position of the femur and tibia is mostly achieved by identifying anatomical landmarks or some form of gap balancing methods. The drawbacks to conventional alignment systems include difficulty with identifying the anatomic landmarks intraoperatively as well as the assumption of standard anatomic relationships, which may not always be consistent across all patients.

Computer-assisted surgery (CAS) was developed to help achieve a more precise and repeatable method. Computer-assisted orthopedic surgery can be either image-based with a preoperative CT or MRI scan; or image-less (without preoperative images), based on anatomic landmarks registered by palpation intra-operatively, and use of a library of scanned images to find a best fit. Conventional computer-assisted orthopedic surgery typically requires manual registration of the bones and the use of trackers for data collection and calibration. The trackers are usually outside of the incision and must be well fixed to the bone because any mobilization can lead to errors in the acquisition of data for the computer assisted database. The acquisition of anatomic landmarks by palpation is manual and surgeon-dependent and not very reproducible.

Prior art navigation techniques typically require "registration" of the bone, which typically involves trackers that are fixed to each bone as a point of reference. The registration process can be time consuming. Surgeons need to be trained to use the registration techniques and adds time to the operation.

SUMMARY OF THE DISCLOSURE

In one implementation, the present disclosure is directed to a method of performing an arthroplasty surgical procedure. The method includes exposing a bone surface and a cartilage surface in an anatomical region of interest; scanning intraoperatively, with an intra-operative 3D scanner, selected landmarks of at least one of the bone or cartilage surfaces; generating, with a processor, from data generated by the 3D scanner during the scanning step, a 3D image; identifying, with the processor, in the 3D image, one or more anatomical landmarks on at least one of the bone and cartilage surfaces; automatically registering, with the processor, the one or more anatomical landmarks to at least one of pre-operative images or a machine learning database of images; calculating, with the processor, according to the identified anatomical landmarks, a plurality of surgical positions; generating, with the processor, guidance information, according to the surgical positions, for guiding the surgical procedure; positioning a bone cutting jig proximate the bone surface, wherein the positioning includes use of the guidance information; and fixing the bone cutting jig to a bone proximate the bone surface.

In another implementation, the present disclosure is directed to a computing device. The device includes an intra-operative 3D scanner and; a processor configured to: receive, from the 3D scanner, scan data from an intra-operative scan of a bone surface in a region of anatomical interest; generate, from the scan data, a 3D image; identify, in the 3D image, one or more anatomical landmarks; calculate, according to the identified anatomical landmarks, a plurality of surgical positions; and generate guidance information, according to the surgical positions, for guiding a surgical procedure.

BRIEF DESCRIPTION OF THE DRAWINGS

These features, aspects, and advantages of the present disclosure will become better understood with regard to the following description and accompanying drawings which illustrate exemplary features of the disclosure. However, it is to be understood that each of the features can be used in the disclosure in general, not merely in the context of the particular drawings, and the disclosure includes any combination of these features, where:

FIG. 1A is a schematic diagram of an example surgical system made in accordance with the present disclosure;

FIG. 1B shows a surgical light that includes a 3D scanner for use with the surgical system of FIG. 1A;

FIG. 1C is a representative 3D image of an anterior view of the distal end of a femur;

FIG. 6A is a schematic of the bone jig of FIG. 5A aligned with projected hologram, positioned on a femur;

FIG. 6B is a schematic of a femur and its mechanical axis;

FIG. 6C is a schematic of a femur and tibia in multiple positions during a method of determining mechanical axes;

DETAILED DESCRIPTION

Aspects of the present disclosure include surgical systems that provide a cost-effective, accurate, and efficient system for performing surgical procedures.

In one aspect of the disclosure, a surgical system utilizes an intra-operative laser, white light or blue light 3D scanner. This 3D scanner is used to determine anatomical landmarks and calculate surgical positions based on such anatomical landmarks. Utilizing well-defined focused light, e.g., laser light lines, onto a bony and/or a cartilage surface, the 3D scanner can be used to generate a complete or partial scan of the surgical surface, which can then superimposed on pre-operative images to instantly register the bone. Such instant registration can be based on pre-operative imaging such as computerized tomography, magnetic resonance imaging, or plane radiographs of the limb or organ. In another aspect, the instant registration can be achieved with machine learning algorithms incorporating artificial intelligence technology.

In another aspect of the disclosure, a surgical system is provided that is useful in performing orthopedic procedures in the absence of trackers. In another aspect of the disclosure, a surgical system is provided that is useful in sizing orthopedic implants in the absence of an implant representative. In another aspect of the disclosure, an artificial intelligence system is used that utilizes machine learning to provide improvements in surgical efficiency. In another aspect of the disclosure, a surgical software system may be used to recognize and track implants, instruments or the like. In another aspect of the disclosure, a specific instrument can be used for calibration and aid in navigation or robotic assistance without trackers.

The present disclosure includes surgical systems that include one or more intra-operative 3D scanners. Although the surgical system is illustrated and described in the context of being useful for orthopedic surgical procedures, the present disclosure can be useful in other instances. Accordingly, the present disclosure is not intended to be limited to the examples and embodiments described herein.

Figure 1D:
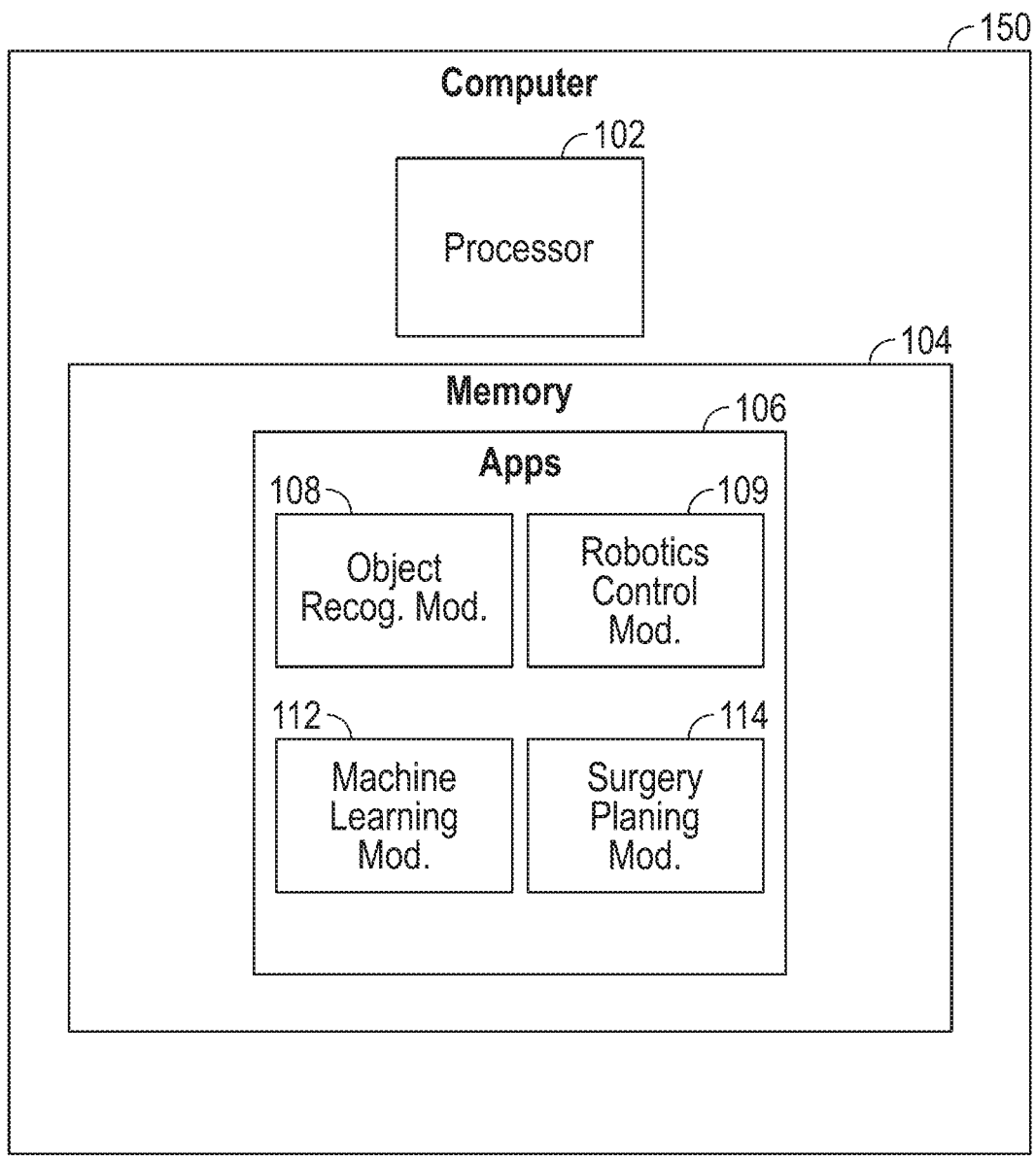
FIG. 1D is a functional block diagram of the computer of FIG. 1A.

FIG. 1A shows a surgical system 100, which can be used to perform a computer-assisted surgery utilizing an intra-operative 3D scanner 110. The surgical system 100 of FIG. 1A is shown in use in an operating room 105 and includes a 3D scanner 110 capable of producing an intra-operative 3D scan of a body part of interest. In the context of FIG. 1A, a patient 115 is undergoing a knee replacement operation. The soft tissue around the knee 120 has been incised to expose the femur 125 and the tibia 130.

The 3D scanner 110 projects a light or other wave 135 onto the region of anatomical interest 140 and monitors the reflection of the light 135 so as produce a 3D scan of the region of interest 140. The 3D scan is transmitted to a computer 150 by cable 155 or by wireless connection. The computer 150 processes and analyzes the 3D scan and controls or assists the surgical procedure based on the analysis, as described below. For example, the computer 150 may control or operate of provide information to an optional robotics unit 160. The robotics unit 160 may perform a computer-guided surgical procedure. Alternatively, the computer 150 may provide information to a surgeon and/or may provide information to the robotics unit 160 that will allow the robotics unit 160 to aid the surgeon during the procedure.

The computer 150 can be any device capable of receiving input, performing calculations based on the input, and producing output as a result of the calculations. The computer 150 may include a central processor 102 that is capable of interacting with a user via a keyboard, a graphical user interface, wireless communication, voice command, or any other manner. The computer 150 may be a personal computer, a laptop, a handheld device, a server, a network of servers, a cloud network, or the like. The user, such as a surgeon or surgeon's assistant, may interact with the computer 150 before, during, or after the surgical procedure. The computer 150 may include a memory 104 or may be otherwise communicatively coupled to a memory that contains various software applications 106 for performing calculations, and executing algorithms, routines, and/or sub-routines, for example, to process information and/or make determinations. For example, the computer 150 may include one or more software applications configured to analyze information obtained from 3D scanner 110, generate a 3D scan, and analyze the 3D scan. In one example, software applications 106 include an object recognition module 108 configured to recognize various objects or features in an image, such as the 3D scanned image. Facial recognition, fingerprint recognition, and iris recognition software systems are examples of object recognition technology. Each of these software systems make comparisons of anatomical features of an image with features in a database that is either stored in the computer 150 or is accessible by the computer by wired or wireless connection. The computer 150 may further include a robotics control module 109 for controlling and communicating with the robotics unit 160. The computer 150 may further include other optional modules, such as an artificial intelligence or also referred to herein as a machine learning module 112 that are configured to apply one or more machine learning algorithms to identify anatomical landmarks of interest.

In one example, the 3D scanner 110 may be a laser, white light or blue light scanner. A 3D scanner is a device that performs surface height measurements of an object using coherence scanning interferometry with broadband light illumination. Commercially available 3D scanners that incorporate 3D scanning technology that may be used or modified for applications of the present disclosure include the AICON PrimeScan and the WLS400M from Hexagon Manufacturing Intelligence in Surrey, Great Britain; the Go!SCAN 3D from Advanced Measurements Labs in Tustin, Calif.; and the HandySCAN 3D™ from Creaform Inc. in Levis, Canada. As shown in FIG. 1B, in one example, the 3D scanner 110 is incorporated into handle 170 of medical light 175. Medical light also includes an array of lights 180 that are used to illuminate the operating room 105 as is known in the art. The 3D scanner 110 also includes one or more light emitting modules that may emit a laser, white light or blue light, that can be projected onto the patient 115 and the area of interest 140. 3D scanner 110 captures reflections of the light emitted by the scanner and which can be used to generate a 3D image using imaging software executed, e.g., by computer 150. In the example shown in FIG. 1B, the 3D scanner 110 is mounted at the center portion of the medical light 175 at or near the handle 170 or in the peripheral aspect of the light 175 so that it may be easily manipulated and directed by a user, such as a surgeon or surgeon's assistant. The user directs the 3D scanner 110 at a region of anatomical interest 140, such as an exposed knee 120, and a 3D scan can be performed to generate a 3D image or model of the anatomy, such as the 3D image 185 shown in FIG. 1C. FIG. 1C shows a 3D image generated from a 3D scan of an anterior view of the distal end of the femur 125. In one example, such images are accurate up to less than 0.001 inches, with up to five million data points generated, e.g., in a few seconds, generating a nearly exact virtual model of the scanned object. The data generated by scanner 110 can be collected efficiently with minimal setups, generated into a 3D image or model using, for example, one or more software modules executed by or accessible by computer 150 As described more below, system 100 may also include a hologram projector 116 for projecting a hologram of an object during surgery, which can be used for a variety of purposes, including projecting a proper position and orientation of a bone cutting jig in a surgical field.

Figure 2:
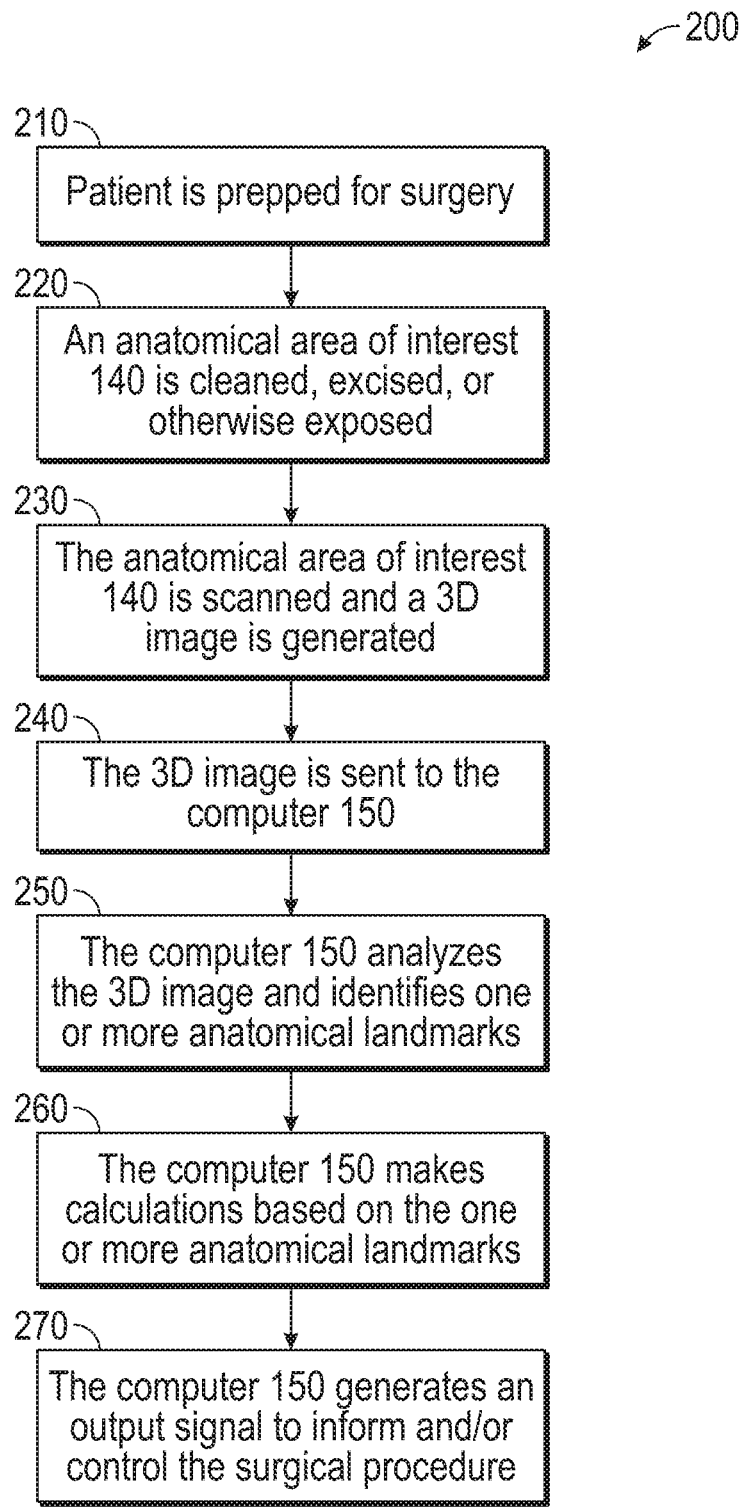
FIG. 2 is a flow chart illustrating an example surgical method.

FIG. 2 illustrates an example of a surgical procedure 200 that may be performed using surgical systems of the present disclosure, e.g., surgical system 100. At step 210, a patient is prepped for surgery. At step 220, the anatomical area of interest 140 is cleaned, excised, or otherwise exposed so that it is visible from the point of view of the 3D scanner 110. Light 135 or other scanning medium is directed onto the anatomical area of interest 140 so that the 3D scanner 110 and/or computer 150 can generate, at step 230, a 3D image of the anatomical area of interest 140. The optical camera of the 3D scanner that is attached to the light handle is communicatively connected to the computer for transmitting images for processing by the object recognition module 108. 3D scanner 110 and object recognition module 108 may be configured to constantly scan a field of view of the 3D scanner camera and automatically detect a scanned surface and anatomical landmarks located thereon. Object recognition module 108 can than automatically match or register the 3D scanner image to a preoperative image of the same anatomical area. If the 3D scanner includes separate processors and software for generating a 3D image, then at step 240, the 3D image is sent to the computer 150 by cable connection 155, by wireless connection, or the like. At step 250, the computer 150 analyses the 3D image, for example, with object recognition module 108, and identifies one or more anatomical landmarks in the image.

The object recognition module 108 can be programmed or configured via a user interface to identify one or more particular anatomical landmarks. Once the one or more anatomical landmarks are identified, at step 260, surgery planning module 114 may be executed to perform calculations and/or make determinations based on the one or more identified anatomical landmarks. For example, surgery planning module 114 can determine the optimal location to make a cut or a drill a hole relative to the anatomical landmark. At step 270 the computer 150, e.g., with surgery planning module 114 can then generate an output signal related to the calculations or determinations. The output signal can be in any of various forms. For example, the output signal can be information that is delivered to the surgeon for the surgeon to consider during performance of the procedure. Alternatively or additionally, the output can be in the form of computer-assisted surgery, and the output can be used to guide pointers, instruments, and the like and/or can be in communication with a robotics module or a robotics unit 160. Alternatively or additionally, the output can be in the form of computer-aided design (CAD) files for use in computer assisted surgery, and the output can be used for providing visual aid on a monitor or other projecting devices, hologram projector 116 onto the surgical field or on the skin or bony surface. The output can be used to guide pointers, instruments, robotic arms, and the like and/or can be in communication with a robotics module or robotics unit 160.

The surgical system 100 of the present disclosure is useful in a wide variety of surgical procedures where precise movements and/or placement of components relative to an anatomical landmark is important. For example, the surgical system 100 is particularly useful in orthopedic procedures where precise cuts and placement of devices is important for the success of the procedure. Joint replacement procedures, such as knee replacement and hip replacement procedures, are examples of such orthopedic procedures. The surgical system 100 is also useful in other surgical arenas, such as guidance of any cutting device. For example, the surgical system 100 can be used for fracture fixation with a plate or other fixation device. The 3D scan can help with superimposing an image onto intra-operative radiographs or fluoroscopic images. The surgical system 100 can also be useful in dental and maxillofacial surgical procedures; in spinal procedures especially when pedicle screws are to be placed by scanning the area and correlating with pre-operative and intra-operative MRI; hand, foot, and ankle procedures, shoulder replacement and fracture treatment procedures. In addition, the surgical system 100 can be useful in general surgical procedures where an organ is scanned by endoscopy and/or laparoscopy, and images are used to guide surgical tools for accurate cut or suture placement and the like.

The surgical system 100 will now be described in the context of a knee replacement procedure. The present examples and the specifics involved are not intended to limit the scope or usefulness of the surgical system 100 but merely to demonstrate its applicability in a particular field. One of ordinary skill in the art will understand that this exemplified use can be modified and extended to other fields, such as any of those mentioned above.

An important factor for a successful knee replacement procedure is the appropriate alignment and placement of implants to reproduce the biomechanical properties of the joint. Determination of proper alignment includes positioning the femur and tibia at a defined angle, typically 90 degrees, to the mechanical axes of the femur and tibia and typically within 3 degrees of error. As such, a cause for a malposition of an implant can be a 3 degree deviation from the 90 degree positioning to the mechanical axis or inappropriate rotation of femoral and/or tibial components. Accordingly, in one example, surgical system 100 may be designed and configured to aid in making the cuts associated with and placement of an artificial knee joint so as to be within the 3 degrees of the desired 90 degree positioning of the implant relative to the mechanical axes of the femur and tibia.

Memory 104 may include information related to the knee joint and the instruments associated with knee joint replacement, such information accessible by object recognition module 108 and surgery planning module 114.

For example, the computer 150 may execute object recognition module 108 and recognize a pre-defined bone jig configured for use in the procedure, as well the anatomy of the knee. After the surgical approach is performed and the knee exposed, the medical lights 175 equipped with a 3D scanner 110 like the one in FIG. 1B may be brought closer to the knee region 120, a 3D scan of the exposed bone can be performed, and a 3D image is generated. In one example, a plurality, e.g., two 3D scanners 110 can be utilized. The plurality of 3D scanners 110 can be positioned at different locations around knee region 120 so that they generate a corresponding plurality of different simultaneous views of the exposed surgical area. The 3D image can then be delivered to the computer 150 by Wi-Fi technology or the like, or data generated by the scanners can be transmitted to the computer to generate a 3D image or model. Object recognition module 108 can be configured to recognize and detect different surface textures and colors and can distinguish between bone, cartilage, instruments, and soft tissue. The 3D image can be analyzed by object recognition module 108 to identify pre-determined anatomical landmarks.

Figure 3A:
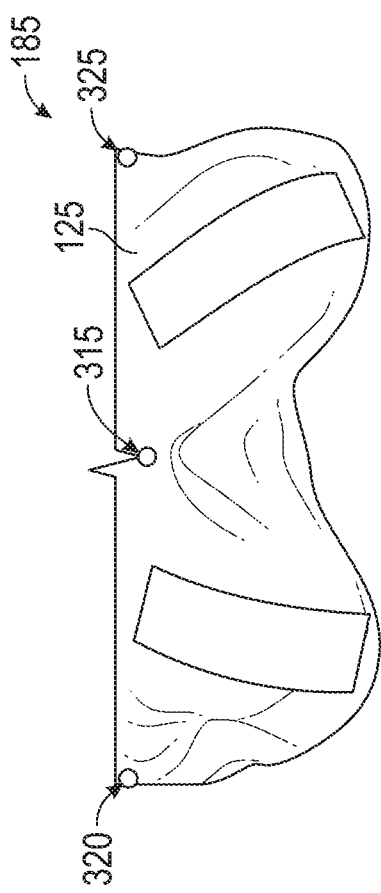
FIG. 3A is a representative 3D image of an anterior view of a distal femur and anatomical landmarks.
Figure 3B:
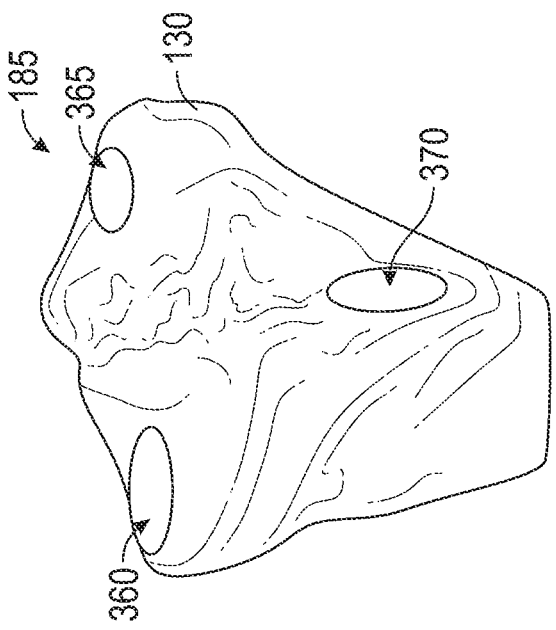
FIG. 3B is a representative 3D image of an enlarged view of the anterior view of a distal femur and anatomical landmarks.
Figure 3C:
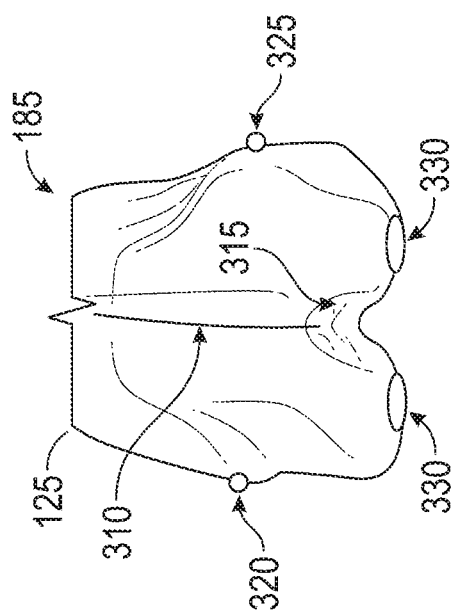
FIG. 3C is a representative 3D image of a top view of the proximal tibia and anatomical landmarks.
Figure 3D:
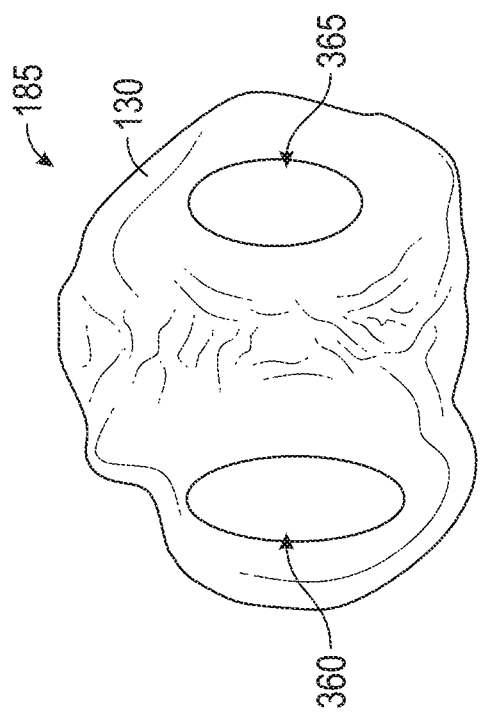
FIG. 3D is a representative 3D image of an anterior view of a proximal tibia and anatomical landmarks.
Figure 4A:
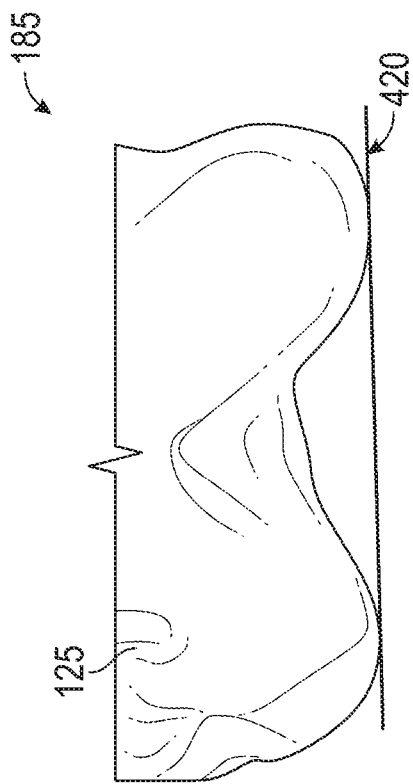
FIG. 4A is a representative 3D image of an anterior view of a distal femur and calculated axes.
Figure 4B:
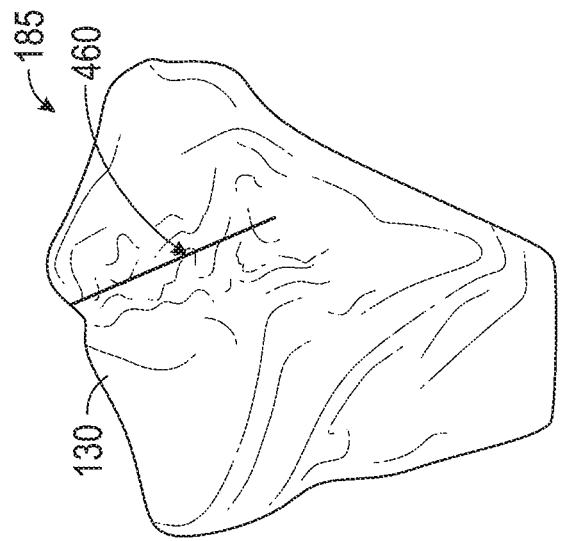
FIG. 4B is a representative 3D image of an enlarged view of the anterior view of a distal femur and calculated axes.
Figure 4C:
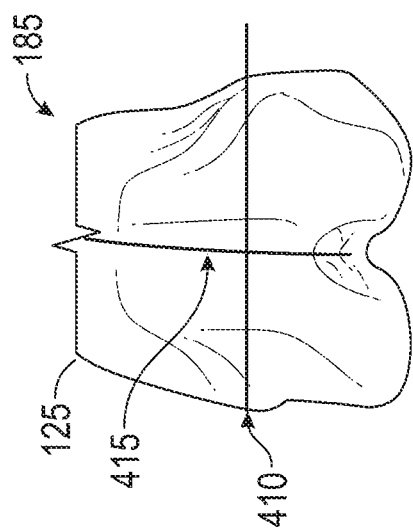
FIG. 4C is a representative 3D image of a top view of the proximal tibia and calculated axes.
Figure 4D:
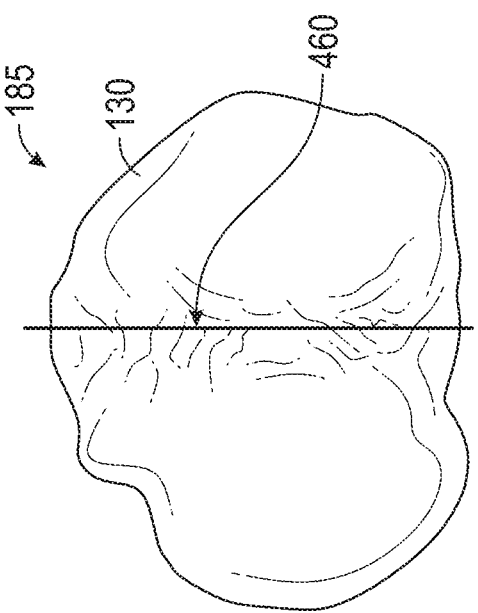
FIG. 4D is a representative 3D image of an anterior view of a proximal tibia and calculated axes.

For the knee replacement surgery, the object recognition module 108 may be configured to identify certain predetermined anatomical landmarks. For example, one or more of bony landmarks, surfaces, limb axes, and dimensions can be identified and defined or recorded by the object recognition module 108 and stored in Memory 104. FIGS. 3A through 3D illustrate examples of the anatomical landmarks that object recognition module 108 may be configured to identify and locate. FIG. 3A is a representative 3D image 185 of an anterior view of the distal femur 125 generated from a 3D scan of the distal femur. FIG. 3B is an enlarged anterior view of a portion of the distal femur 3D image 185. FIG. 3C is a representative 3D image 185 of a top view of the proximal tibia 130. FIG. 3D is a representative 3D image 185 of an anterior view of the proximal tibia 130. On the femur 125, object recognition module 108 may be configured to identify one or more of the trochlea groove 310, the trochlea notch 315, the medial epicondyle 320, the lateral epicondyle 325, and the distal femur articulating surface 330. On the tibia 130, object recognition module 108 may be configured to identify one or more of the medial tibial plateau 360, the lateral tibial plateau 365, and the tibial tubercle 370. In another example, object recognition module 108 may be configured to identify one or more predetermined bone-cartilage junctions as one of the anatomical landmarks. In one example, the computer 150 may be used to identify and locate all of the above landmarks on the femur 125 and the tibia 130.

Figure 5A:
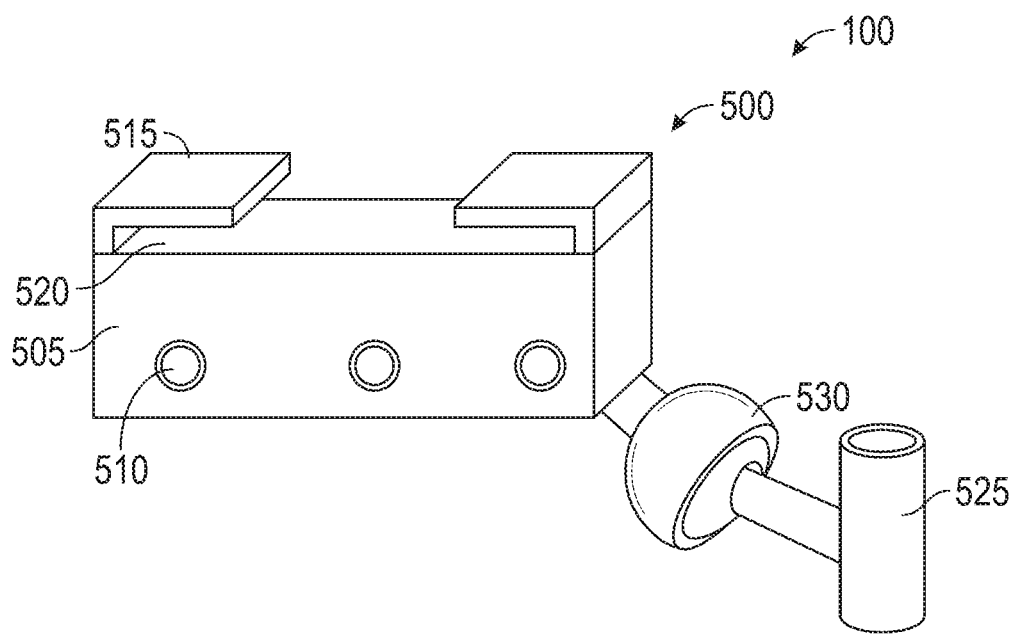
FIG. 5A is a bone jig for use in the surgical system of FIG. 1A.
Figure 5B:
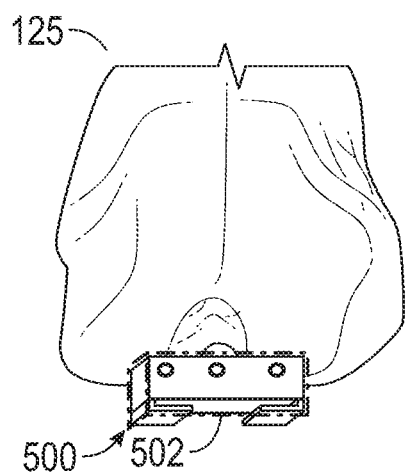
FIG. 5B is a schematic showing the bone jig of FIG. 5A positioned and aligned with a projected hologram of an outer perimeter of the bone jig, on a femur.
Figure 5C:
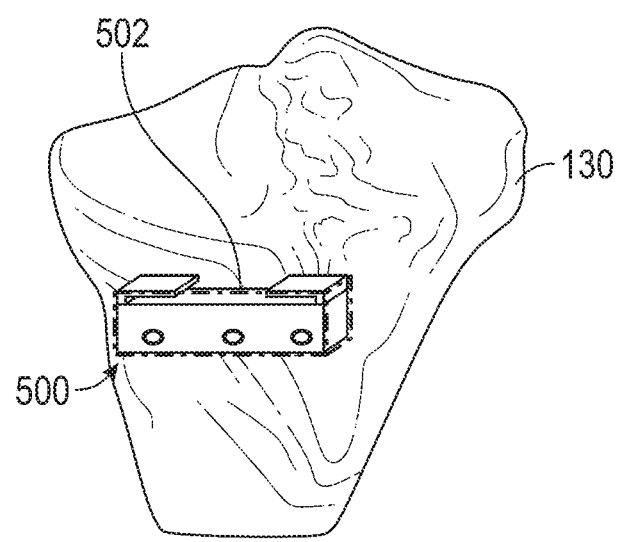
FIG. 5C is a schematic showing the bony jig of FIG. 5A positioned and aligned with a projected hologram of an outer perimeter of the bone jig, on a tibia.

After identifying and locating the anatomical landmarks, surgery planning module 114 may be executed to perform calculations based on the landmarks. For example, FIGS. 4A through 4D show the representative 3D images 185 from FIGS. 3A through 3D respectively, and also illustrate pre-established axes calculated by surgery planning module 114 for implant positioning. On the distal femur 125, surgery planning module 114 may calculate the transepicondylar axis (TEA) 410, the patellofemoral axis (PFA) 415, and the posterior condylar axis (PCA) 420. On the proximal tibia 130, surgery planning module 114 may calculate the tibial rotation axis (TRA) 460. In one example, surgical system 100 further includes a bone jig 500 (FIG. 5A). In the illustrated example, bone jig 500 is a bone cutting guide and memory 104 may contain one or more dimensions of the jig. The bone jig has a body 505 with pin holes 510 for fixation to the bone. A saw blade protector 515 helps define a guide slot for a saw blade. Bone jig 500 also includes an initial fixation pin hole 525 coupled to body 505 by a hinged connection 530, which as described below, can be used for fine adjustments of the bone jig 500 prior to fixation of the jig to the bone with pin holes 510. The bone jig 500 is relatively small and is user friendly. The bone jig 500 is positioned over the femur 125 in FIG. 5B and over the tibia 130 in FIG. 5C at precisely determined positions as will be described. FIGS. 5B and 5C also illustrate a hologram projection 502 projected onto the bony surface from hologram projector 116 and show the jig aligned with the projection. In the illustrated example, the projection is a projection of a portion of an outer perimeter of the bone jig. In other examples, other types of projections may be used, such as the projection of one or more points. The jig position can, therefore, be projected onto the bony surface, so that the surgeon can position the jig with the projected hologram. As will be appreciated, hologram projector 116 can also be configured to project other holograms, for example, one or more targets or a portion of an outer perimeter of other jigs. In other example, rather than aligning a bone cutting jig, such as jig 500, with a hologram, such as hologram 502, a hologram projection may be directly used as an augmented reality cutting guide and a surgeon may use a surgical instrument, such as a saw in a plane of cut that is projected by the hologram.

Since the bone jig 500 has exact pre-determined dimensions, it can also be used by the computer 150, e.g., surgery planning module 114, to calibrate images (for example, in cases where there are no pre-operative images) of the bone jig captured by 3D scanner 110. The bone jig 500 parameters and dimensions are loaded into the computer 150 and stored in Memory 104 prior to surgery. Then, during surgery, object recognition module 108 can be configured to detect the unique shape and dimensions of bone jig 500 and, in some examples, since the dimensions are already defined, the dimensions can be used to calibrate the image of the scanned bone adjacent to the bone jig. With the jig 500 roughly positioned in a region of interest, a pin can be inserted through the initial fixation pin hole 525 and the bone jig 500 is placed over the bone and the bone jig 500 can be provisionally fixed by this pin to the bone (as shown in FIG. 6A). The computer 150 recognizes the bone jig 500, the 3D image of the bone, and the calibrated bone.

The mechanical axis 610 of the femur and the mechanical axis 620 of the tibia are determined as shown in FIGS. 6A through 6C. With jig 500 provisionally fixed to the bone, the knee can be placed in different positions, moved around in a triangle 630 until the mechanical axis of the bone is identified from this triangular positioning. This is done based on the shape of the cutting jig, distance and position as referenced to the optical camera of 3D scanner 110, e.g., on the light handle 170. Bone jig position data can be determined from the image data captured by the camera of the 3D scanner 110 with, e.g., surgery planning module 114, and stored in Memory 104. Surgery planning module 114 may also be configured to calculate the femur mechanical axis from the bone jig position data. The rotational axis of the femur can also be calculated based on transepicondylar axis or gap balancing principles, which are previously described and well-known in the art. Since the mechanical axis of the femur 125 goes through the femoral head, by rotating the distal aspect of the femur in various positions, the position and orientation of the bone jig 500 and the bony surface can be determined from images of the jig and bone surface captured by the camera of the 3D scanner 110, and the computer 150, with, e.g., surgery planning module 114, can generate a model that defines the femur mechanical axis. This axis is used for cutting the distal femur 125. Similarly, the tibial mechanical axis is defined based on the change in position and orientation of the jig 500 fixed to the proximal tibia, determined from analysis of images of the jig captured by the optical camera of the 3D scanner while the tibia is rotated around the ankle axis. These axes are important for proper implant positioning as the bony cuts and thus the implants are desirably placed 90 degrees to the mechanical axes 610, 620. After the mechanical axis of the femur 610 and the mechanical axis of the tibia 620 are defined, surgery planning module 114 can determine the proper positions of the bone jig 500 over the bony surface. Surgery planning module 114 can also be configured to generate an image of the proper position of the jig on the bone that can be overlaid with a live image of the bone surface displayed on a monitor of computer 150. The surgeon can adjust the position and orientation of the jig on the bone surface while watching the monitor until the live image of the jig is aligned with the properly-positioned image generated by the surgery planning module 114. In some examples, hologram projector 116 may also be used to project a hologram of a properly-positioned jig on the bone surface, which the surgeon can use to align jig 500. The calculated jig position and orientation can be modified based on the surgeon's preferences and techniques and can also be modified pre- and intra-operatively to accommodate different bony resection methods (measured resection, gap balancing and kinematic or a combination thereof). The jig position and orientation can also be pre-defined based on the surgeon's preferences and techniques.

Figure 7A:
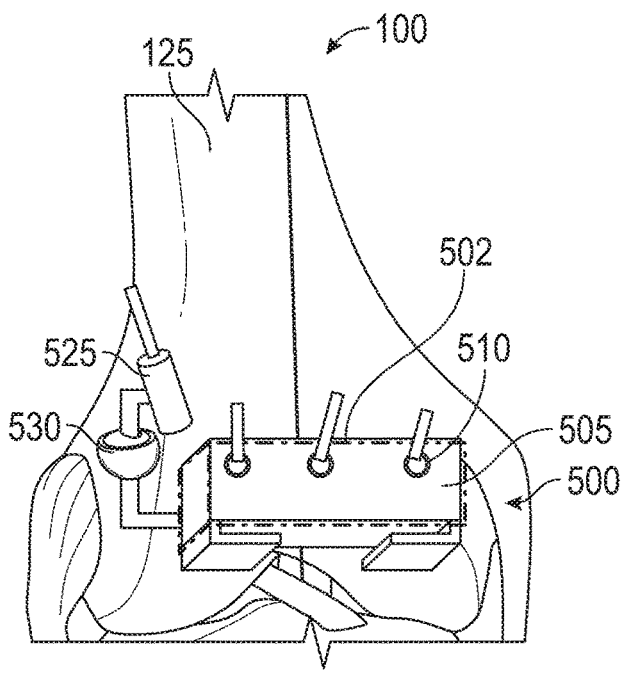
FIG. 7A is a schematic of the bone jig of FIG. 5A positioned and aligned with a projected hologram of an outer perimeter of the bone jig, on a femur relative to the mechanical axis.
Figure 7B:
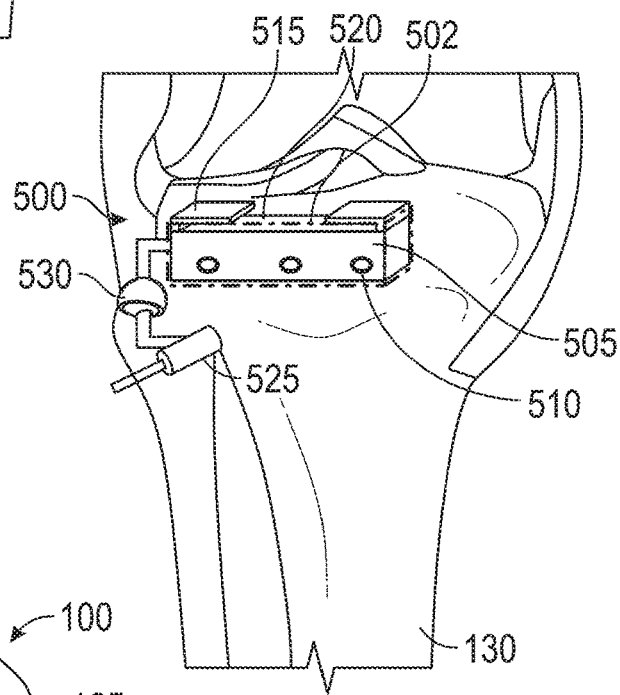
FIG. 7B is a schematic of the bone jig of FIG. 5A positioned on a tibia.
Figure 7C:
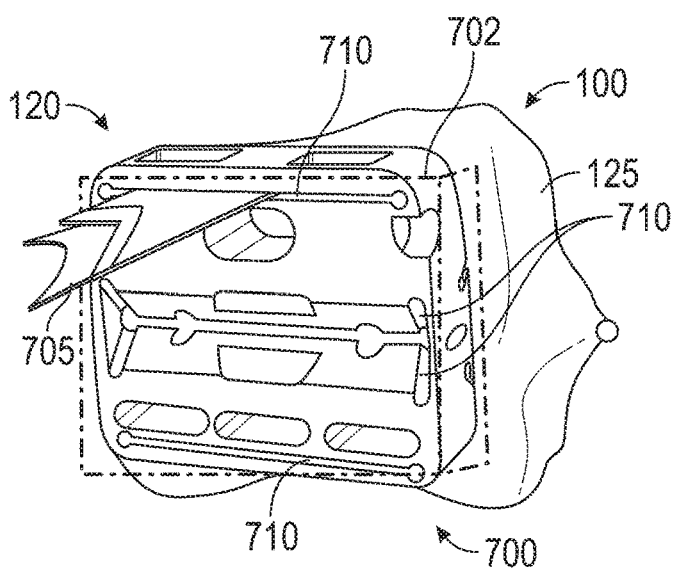
FIG. 7C is a schematic showing a femoral cutting jig aligned with a projected hologram of the femoral cutting jig, positioned on a femur.

As shown in FIGS. 7A through 7C, surgery planning module 114 can be executed to calculate the optimum position of the bone jig 500 for restoration of bony cut in three planes: Medial-lateral, anterior-posterior, and superior-inferior planes. For the femoral cut, as shown in FIG. 7A, surgery planning module 114 may determine the perpendicular axis to the mechanical axis of the femur and calculate the position of the jig to obtain appropriate depth of bony resection, as well as alignment in three planes. The bone jig 500 can then be fixed to the femur 125 with multiple pins using the methods described above, e.g., when the bone jig 500 is superimposed accurately on a projected hologram from hologram projector 116 and the surgeon has achieved all the qualifying criteria for the bony cut (which are based on principles of knee arthroplasty), including depth of the cut and the location of the cut in the three planes. Alternatively, the surgeon can watch a live images of the knee region that includes a computer generated cutting jig in the proper position and orientation.

Figure 8A:
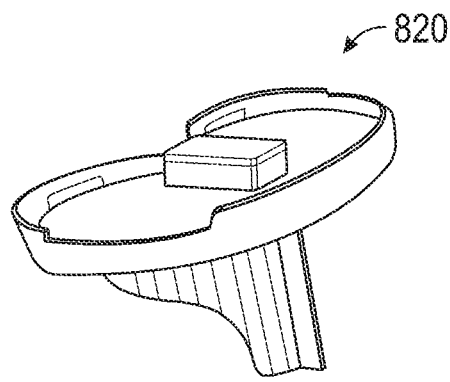
FIG. 8A is an illustration of an example of a tibial implant.
Figure 8B:
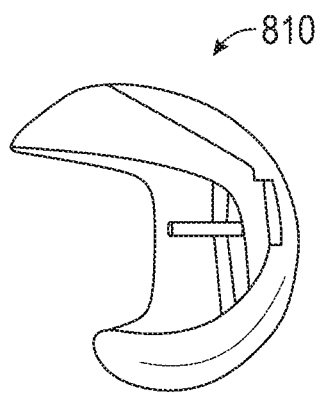
FIG. 8B is an illustration of an example of a femoral implant.
Figure 8C:
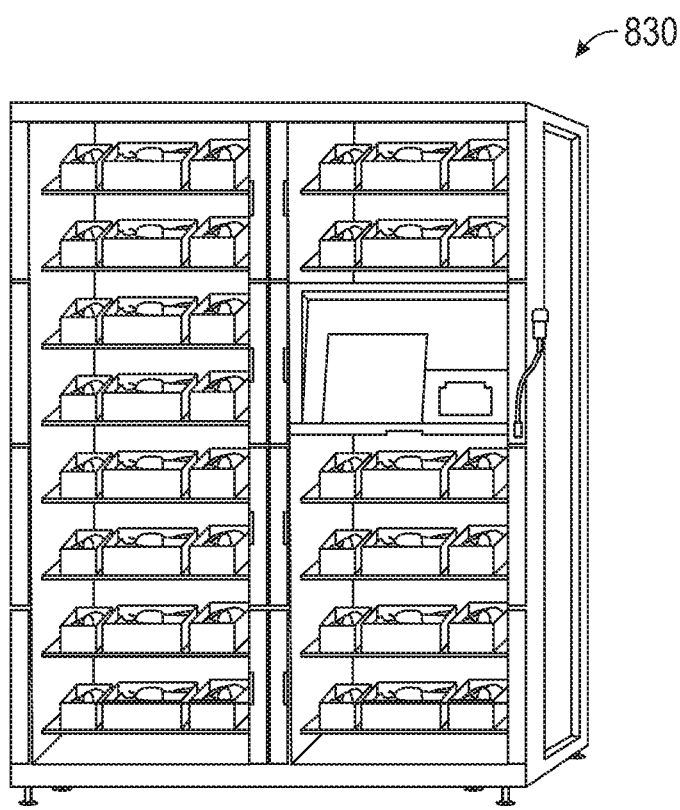
FIG. 8C is an illustration of an example of an implant dispensing machine.

FIG. 7B shows the jig positioned for the tibial cuts. After the proximal tibia and distal femoral cuts, the bone cutting jig(s) 500 are removed but the initial pins can be left in place. Then a spacer block (not illustrated) can be placed in the knee 120 in extension. The soft tissue balance of knee is assessed in extension with varus/valgus forces manually applied. Scanner 110 can continuously monitor the movement of the pins during the varus/valgus test and the change in position of the pins can be calculated by the computer 150, e.g., surgery planning module 114, which can be used to determine the medial and lateral opening in extension. This opening is usually 2-4 mm. If the extension gap is not balanced, the surgeon can perform various methods known in the art to achieve a balanced extension gap. Then the knee is placed in 90 degrees of flexion and distracted by manual means or use of lamina spreaders. The femoral 4-in-1 cutting jig 700, which is typically provided by the implant manufacturing company and specific to the size of the implant is placed over the distal femoral cut. The rotational orientation of the femoral 4-in-1 cutting jig 700 can be determined based on anatomic landmarks identified by object recognition module 108 and re-creation of a rectangular flexion gap. The computer 150 has the ability to identify this instrument and communicate with the surgeon as displayed on the monitor or hologram projector, as what the appropriate position should be to achieve a balanced flexion gap. Femoral sizing can be performed by surgery planning module 114 based on implant dimensions stored in Memory 104 for femoral implants 810, such as the one shown in FIG. 8B, bony landmarks that were identified previously and stored in memory and the calculated flexion gap. In one example, the flexion gap is achieved by "parallel to the tibial cut" technique, distracting the femur in 90 degrees of flexion. Femoral sizing and rotation can be adjusted intra-operatively if the surgeon needs to up or downsize the implant to achieve accurate flexion and extension gaps. The tibial implant is them similarly sized for tibial implant 820. After cutting the anterior, posterior, chamfers using a bone saw 705 inserted into the cutting slots 710 in the 4-in-1 cutting jig 700 as shown in FIG. 7C (the alignment of the 4-in-1 cutting jig 700 being guided by hologram 702), trial implants are used to assess the gaps and alignment prior to opening the final implants. surgery planning module 114 can determine the correct size of the trial implants and communicate with an implant dispensing machine 830, as shown in FIG. 8C, to open the appropriate door for implant and reduce errors. Computer 150 can also send an email for replenishment and a bill after the implant is used.

The implant dispensing machine 830 can be operated by, e.g., nurses in an operating room and can eliminate the need to have an implant representative present in the operating room for routine cases. The ability to integrate the surgical system 100 and a facility's billing department can also be beneficial.

In the illustrated example, the implant dispensing machine 830 includes actual implants provided by one or more manufacturing companies and the machine is replenished by the corresponding companies. Implant dispensing machine 830 can also store disposable items such as instruments and jigs.

Although described in this example in the context of a knee replacement operation, the surgical system 100 can be similarly used in hip replacement and shoulder replacement procedures, as well as other procedures mentioned above.

In hip replacement procedures, the surgical system 100 can calculate functional anteversion and abduction angles in adjusted zone. The computer 150 can feature broach recognition, femoral anteversion and depth of broach based on pin location. The surgical system 100 allows for only one reamer to be necessary during pelvic preparation, provides depth of ream, anteversion and abduction angles for final cup positioning. Lastly, the surgical system 100 can capture the final data and store on the patient's file and generates operative report for better documentation.

In one example, system 100 can be used to perform a surgery without conventional instruments, traditional manual alignment jigs, pre-operative CT scans, trays, or sterilization of multiple trays during surgery, which can significantly increase OR efficiencies and thus simplify knee and hip surgeries. In other examples, system 100 can be used in combination with one or more of the above to improve the accuracy and efficiency of a surgery.

The surgical system 100 of the present disclosure provides an accurate, affordable, easy to use open-platform navigation system for reproducible and correctly-performed hip and knee replacement or other surgical procedures. The surgical system 100 can be used to eliminate one or more of current traditional instruments, can make a surgery less complicated, eliminate trays, sterilization processes and reduce costs while improving outcomes. The surgical system 100 can also be used to improve the surgical flow and make a surgery faster with less errors. In addition, implant dispensing machines such as implant dispensing machine 830 can reduce errors in implant utilization by eliminating human errors, improve billing processes and provide for auto-replenishment of implants The surgical system 100 uses 3D intra-operative laser, white, or blue light scanners attached to a medical light above a patient. In one example, the system obviates the need for trackers, which are typically used in prior art computer-aided navigation to aid with registration as a fixed point on the bone.

Aspects of the present disclosure also include, in one example, a method of performing a surgical procedure, comprising: scanning, with a 3D scanner, a region of anatomical interest; generating, with a processor, from data generated by the 3D scanner during the scanning step, a 3D image; identifying, with the processor, in the 3D image, one or more anatomical landmarks; calculating, with the processor, according to the identified anatomical landmarks, a plurality of surgical positions; and generating, with the processor, guidance information, according to the surgical positions, for guiding a surgical procedure.

Aspects of the present disclosure also include a computing device, comprising: a 3D scanner and; a processor configured to: receive, from the 3D scanner, scan data from a scan of a region of anatomical interest; generate, from the scan data, a 3D image; identify, in the 3D image, one or more anatomical landmarks; calculate, according to the identified anatomical landmarks, a plurality of surgical positions; and generate guidance information, according to the surgical positions, for guiding a surgical procedure.

Aspects of the present disclosure also include:

This surgical system is useful in performing orthopedic procedures in the absence of trackers.

A surgical system utilizes an intra-operative laser 3D scanner

This 3D laser scanner is used to determine anatomical landmarks and calculates surgical positions based on the anatomical landmarks This "instant registration" can be based on pre-operative imaging such as computerized tomography, magnetic resonance imaging, or plane radiographs of the limb or organ.

In another aspect, the instant registration is based on machine learning and artificial intelligence.

An object recognition module that includes code, algorithms and/or routines, allows for identification of the actual surfaced area based on the 3D scan This software recognizes the scanned bone and determines a proper placement of a pin for which all calculations are based on, for example one pin is placed on the femur and one on the tibia during a knee replacement.

The software can recognize the distance change between the two pins, which is used for soft-tissue assessment.

This software system is used to recognize and track the implants, instruments or the like.

The object recognition module can also recognize the cutting jigs/instruments.

The computer screen can show the plane of the bony cut so the surgeon can align the jig and the cutting planes.

An implant dispensing machine that can store multiple sizes of an implant.

A computer that can identify the size of implant trials and communicate with an implant dispensing machine to open an appropriate door for a specified implant and reduce errors.

The foregoing has been a detailed description of illustrative embodiments of the invention. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method of performing an arthroplasty surgical procedure, comprising:
   exposing a bone surface and a cartilage surface in an anatomical region of interest;
   scanning intraoperatively, with an intra-operative 3D scanner, selected landmarks of at least one of the bone or cartilage surfaces;
   generating, with a processor, from data generated by the 3D scanner during the scanning step, a 3D image;
   identifying, with the processor, in the 3D image, one or more anatomical landmarks on at least one of the bone and cartilage surfaces;
   automatically registering, with the processor, the one or more anatomical landmarks to at least one of pre-operative images or a machine learning database of images;
   calculating, with the processor, according to the identified anatomical landmarks, a plurality of surgical positions;
   generating, with the processor, guidance information, according to the surgical positions, for guiding the surgical procedure;
   positioning a bone cutting jig proximate the bone surface, wherein the positioning includes use of the guidance information;
   fixing the bone cutting jig to a bone proximate the bone surface;
   capturing, with an image capture device, a plurality of images of the bone cutting jig provisionally fixed to the bone as the bone cutting jig and region of anatomical interest are moved;
   determining, with the processor, positions of the bone cutting jig from the plurality of images; and
   calculating, with the processor, from the determined positions, a mechanical axis of a bone.

2. The method of claim 1, wherein the 3D scanner is one or more of a laser, white light, or blue light 3D scanner.

3. The method of claim 1, wherein the scanning step includes performing surface height measurements of the bone surface using coherence scanning interferometry with broadband light illumination.

4. The method of claim 1, wherein the bone surface is a distal femur or a proximal tibia.

5. The method of claim 1, wherein the identifying step includes comparing, with the processor, the 3D image to one or more pre-operative images to identify the anatomical landmarks.

6. The method of claim 1, wherein the identifying step includes comparing, the processor executing a machine learning software module, the 3D image to a training database of images to identify the anatomical landmarks.

7. The method of claim 1, wherein the one or more anatomical landmarks include one or more of a trochlea groove, a trochlea notch, a bone-cartilage junction, a medial epicondyle, a lateral epicondyle, a distal femur articulating surface, a medial tibial plateau, a lateral tibial plateau, or a tibial tubercle.

8. The method of claim 1, wherein the surgical positions include one or more of a transepicondylar axis, a patellofemoral axis, a posterior condylar axis, or a tibial rotation axis.

9. The method of claim 1, wherein the calculating of the surgical positions includes calculating the surgical positions according to the calculated mechanical axis, the positioning step including positioning the provisionally-fixed jig according to the guidance information prior to securely fixing the jig to the bone surface for performing a cut.

10. The method of claim 1, wherein the mechanical axis is at least one of a femur or tibia mechanical axis.

11. The method of claim 1, wherein the generating step includes displaying, on a graphical user interface, a live video of the anatomical region of interest and a computer-generated image of a target in a determined position and orientation relative to the anatomical region of interest according to the calculated surgical positions, the positioning step including positioning the bone cutting jig to align with the target.

12. The method of claim 1, wherein the generating step includes projecting onto the anatomical region of interest, with a hologram projector, a hologram of a target in a determined position and orientation relative to the anatomical region of interest according to the calculated surgical positions, the positioning step including positioning the bone cutting jig to align with the target.

13. The method of claim 12, wherein the hologram of a target is a hologram of the bone cutting jig.

14. The method of claim 1, wherein the anatomical region of interest is a knee, the method further comprising:
   performing proximal tibia and distal femoral cuts;
   removing the bone cutting jig while leaving at least one pin used to secure the bone cutting jig; capturing a plurality of images of the knee and the at least one pin during application of varus and valgus forces; and
   determining, with the processor, from the plurality of images, a soft tissue balance of the knee.

15. The method of claim 14, further comprising:
   determining, with the processor, from the 3D image, at least one of a target position and orientation of a femoral 4-in-1 cutting jig;
   generating, with the processor, guidance information, according to the determined target position and orientation of the femoral 4-in-1 cutting jig;
   placing the knee in flexion; placing the femoral 4-in-1 cutting jig over the distal femoral cut; and
   positioning the femoral 4-in-1 cutting jig, wherein the positioning includes use of the femoral 4-in-1 cutting jig guidance information.

16. The method of claim 1, further comprising:
   sending an instruction, with a processor, to an implant dispensing machine that contains a plurality of implants of varying size or type, to dispense an implant having a specified characteristic; and
   in response to receiving the instruction, opening, with the implant dispensing machine, a secured compartment containing the implant.

17. The method of claim 1, wherein the method does not include use of trackers fixed to bone for data collection, calibration, or navigation.

18. The method of claim 1, wherein the method does not include or require a manual registration process.

* * * * *